(12) United States Patent
Newcomb et al.

(10) Patent No.: US 9,782,061 B2
(45) Date of Patent: Oct. 10, 2017

(54) VIDEO LARYNGOSCOPY DEVICE

(71) Applicant: Velosal Medical, Inc., Cary, NC (US)

(72) Inventors: David Newcomb, Morrisville, NC (US); Michael George Gonzalez, Houston, TX (US)

(73) Assignee: Velosal Medical, Inc., Cary, NC (US)

( * ) Notice: Subject to any disclaimer, the term of this patent is extended or adjusted under 35 U.S.C. 154(b) by 0 days.

(21) Appl. No.: 15/061,517

(22) Filed: Mar. 4, 2016

(65) Prior Publication Data

US 2016/0256047 A1    Sep. 8, 2016

Related U.S. Application Data

(60) Provisional application No. 62/128,448, filed on Mar. 4, 2015.

(51) Int. Cl.
| | | |
|---|---|---|
| *A61B 1/267* | (2006.01) | |
| *A61B 1/06* | (2006.01) | |
| *A61B 1/12* | (2006.01) | |
| *A61B 1/015* | (2006.01) | |
| *A61B 1/05* | (2006.01) | |
| *A61B 1/00* | (2006.01) | |

(52) U.S. Cl.
CPC .......... *A61B 1/267* (2013.01); *A61B 1/00016* (2013.01); *A61B 1/00052* (2013.01); *A61B 1/015* (2013.01); *A61B 1/05* (2013.01); *A61B 1/0676* (2013.01); *A61B 1/0684* (2013.01); *A61B 1/126* (2013.01); *A61B 1/00103* (2013.01)

(58) Field of Classification Search
CPC ........................ A61B 1/267–1/2676
USPC .................................................. 600/185–200
See application file for complete search history.

(56) References Cited

U.S. PATENT DOCUMENTS

| | | | |
|---|---|---|---|
| 6,890,298 B2 | 5/2005 | Berci et al. | |
| 7,946,981 B1 * | 5/2011 | Cubb ................. | A61B 1/00052 600/120 |
| 7,988,622 B2 | 8/2011 | Achas Gandarias | |
| 8,029,440 B2 | 10/2011 | Birnkrant et al. | |
| 8,366,612 B2 | 2/2013 | Rosenthal | |
| 8,529,442 B2 | 9/2013 | Pacey et al. | |
| 8,652,033 B2 | 2/2014 | Berci et al. | |
| 8,864,657 B2 | 10/2014 | Tydlaska | |
| 8,888,683 B2 | 11/2014 | Mejia | |
| 2001/0032646 A1 * | 10/2001 | Christopher ...... | A61M 16/0488 128/200.26 |
| 2006/0020171 A1 | 1/2006 | Gilreath | |
| 2007/0179342 A1 | 8/2007 | Miller et al. | |

(Continued)

FOREIGN PATENT DOCUMENTS

| | | |
|---|---|---|
| WO | WO 2014/184795 | 11/2014 |
| WO | WO 2014/191773 | 12/2014 |

OTHER PUBLICATIONS

Bernard, David, "Video Views of Airway Visualization Devices", Outpatient Surgery Magazine, Sep. 2014, 2 pages.

(Continued)

*Primary Examiner* — Nicholas Plionis
(74) *Attorney, Agent, or Firm* — Myers Bigel, P.A.

(57) ABSTRACT

A video laryngoscopy device includes: a blade having a handle and a blade portion extending from the handle; an electronics housing extending from the blade portion; and a camera or image sensor and a lighting element housed within the electronics housing. The device may be single use disposable.

16 Claims, 9 Drawing Sheets

(56) References Cited

U.S. PATENT DOCUMENTS

| | | | |
|---|---|---|---|
| 2008/0029100 A1* | 2/2008 | Glassenberg | A61B 1/04 128/207.15 |
| 2008/0064926 A1 | 3/2008 | Chen | |
| 2009/0247833 A1 | 10/2009 | Tanaka | |
| 2011/0130627 A1 | 6/2011 | McGrail et al. | |
| 2011/0319716 A1* | 12/2011 | Naito | A61B 1/00091 600/157 |
| 2012/0172664 A1* | 7/2012 | Hayman | A61B 1/00045 600/109 |
| 2013/0057667 A1 | 3/2013 | McGrath | |
| 2013/0197312 A1 | 8/2013 | Miller et al. | |
| 2013/0296653 A1* | 11/2013 | Brown | A61M 16/06 600/114 |
| 2013/0303849 A1* | 11/2013 | Allyn | A61B 1/00045 600/109 |
| 2013/0310650 A1 | 11/2013 | Hales et al. | |
| 2014/0160261 A1 | 6/2014 | Miller et al. | |

OTHER PUBLICATIONS

Holm-Knudsen, Rolf, "The different pediatric airway—a review of new devices for indirect laryngoscopy in children younger than two years of age", Pediatric Anesthesia, Nov. 6, 2010, 6 pages.

"Critical Care Medicine; First Video Laryngoscopic Intubation Performed via Telemedicine", Medical Devices & Surgical Technology Week, Oct. 18, 2009, 3 pages.

"Airtrac guided Video intubation", Airtrac, Feb. 12, 2015, 1 page.

\* cited by examiner

TO IMAGE SENSOR

VIDEO LARYNGOSCOPY DEVICE

RELATED APPLICATIONS

This application claims priority from U.S. Provisional Application No. 62/128,448, filed Mar. 4, 2015, the disclosure of which is hereby incorporated herein in its entirety.

BACKGROUND OF THE INVENTION

The present invention relates to video laryngoscopy and, more particularly, to a video laryngoscopy device.

Currently, devices used for video laryngoscopes are costly. Components for these devices require sterilization.

As can be seen, there is a need for a video laryngoscopy device that may be intended as a single use disposable device in which no components require sterilization.

SUMMARY

Some embodiments of the present invention are directed to a video laryngoscopy device including: a blade having a first end and a second end; a screen connected to the first end of the blade; an internal camera module attached to the second end of the blade; a plurality of lighting elements attached to the second end of the blade; and a protective cover shield enclosing the camera module and the lighting element. The device may be single-use disposable. The protective cover shield may include one or more features to inhibit or prevent substances from adhering to an external surface thereof.

Some other embodiments of the present invention are directed to a video laryngoscopy device including: a blade having a handle and a blade portion extending from the handle; an electronics housing extending from the blade portion; and a camera or image sensor and a lighting element housed within the electronics housing. The device is single use disposable.

According to some embodiments, the blade is in communication with a display screen, and the display screen is configured to display video from image data communicated by the blade. The blade may be in wireless communication with the display screen and may be configured to communicate the image data via a Bluetooth wireless connection.

According to some embodiments, a protective cover shield extends away from the electronics housing, with the protective cover shield defining a cavity in front of the image sensor and the lighting element. At least one hole may be defined in the protective cover shield, and the at least one hole may be aligned with at least one of the image sensor and the lighting element. The at least one hole may include a plurality of holes, with one each aligned with the image sensor and the lighting element. The protective cover shield may be dome shaped. The protective cover shield may include additives therein or thereon configured to repel debris.

According to some embodiments, a camera lens cleaning mechanism is configured to inject air to the image sensor and/or to the cavity to thereby remove debris on a lens of the image sensor. A push button may be on a top portion of the handle, and the camera lens cleaning mechanism may be configured to inject the air responsive to actuation of the push button. The camera lens cleaning mechanism may include an air reservoir, a nozzle connected to the air reservoir and tubing connected to the nozzle and terminating at or adjacent the image sensor and/or the cavity. Air from the air reservoir may be injected through the nozzle and through the tubing responsive to actuation of the push button.

According to some embodiments, the camera lens cleaning mechanism includes a first check valve disposed between the air reservoir and the nozzle, with the first check valve configured to allow the flow of air toward the image sensor and/or to the cavity through the tubing and prevent the flow of air in the opposite direction. According to some embodiments, a filter is provided on a sidewall of the handle, the camera lens cleaning mechanism includes a second check valve on a bottom portion of the air reservoir, with the second check valve configured to allow the flow of air from outside the handle through the filter into the air reservoir and prevent the flow of air in the opposite direction.

According to some embodiments, the electronics housing includes: a first ramped portion extending away from a surface of the blade portion and away from a distal end of the blade portion; a straight portion extending away from the first ramped portion and including a first aperture aligned with the image sensor and a second aperture aligned with the lighting element; a second ramped portion extending away from the straight portion and away from the distal end of the blade portion; and a rounded portion on each opposite side of the first ramped portion, straight portion and second ramped portion. The image sensor and the lighting element may be held on a substrate in the electronics housing, and the electronics housing may include a partition member between the image sensor and the lighting element. The image sensor may be a cube camera that extends further away from the substrate than does the lighting element. The cube camera may include a lens that is substantially flush with a front surface of the straight portion.

Further features, advantages and details of the present invention will be appreciated by those of ordinary skill in the art from a reading of the figures and the detailed description of the preferred embodiments that follow, such description being merely illustrative of the present invention.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a device useful in tracheal intubation. More specifically, an exemplary embodiment of the present invention provides a video laryngoscopy device designed for single use. The video laryngoscopy device may include a camera module which may be partially protected while also being directly exposed to the field of view in order to eliminate the need for temperature sensing and anti-fog elements. In certain embodiments, a protected covering shield may be adapted so that an image sensor may be fully protected while not being directly exposed to the field of view by incorporating a geometry which may minimize fog or debris in the portion of the covering that is related to the field of view. An embodiment of the video laryngoscopy device may include infrared and visible lighting. In certain embodiments, the video laryngoscopy device may include lighting of desired wavelengths and may employ a light filter.

Figure 1:
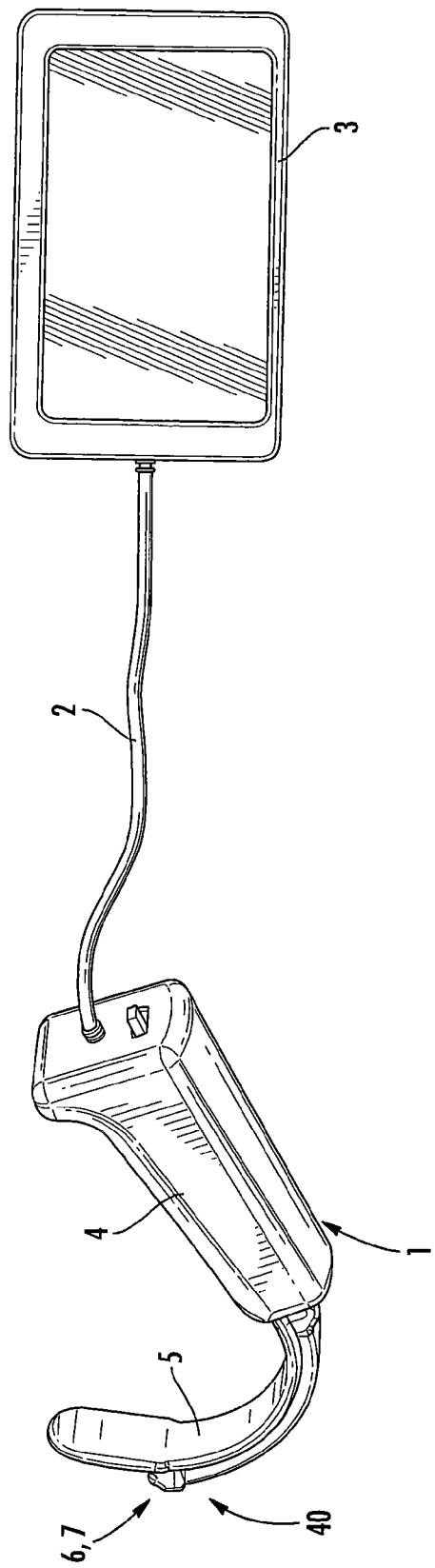
FIG. 1 is a perspective view of an exemplary embodiment of the present invention.
Figure 2:
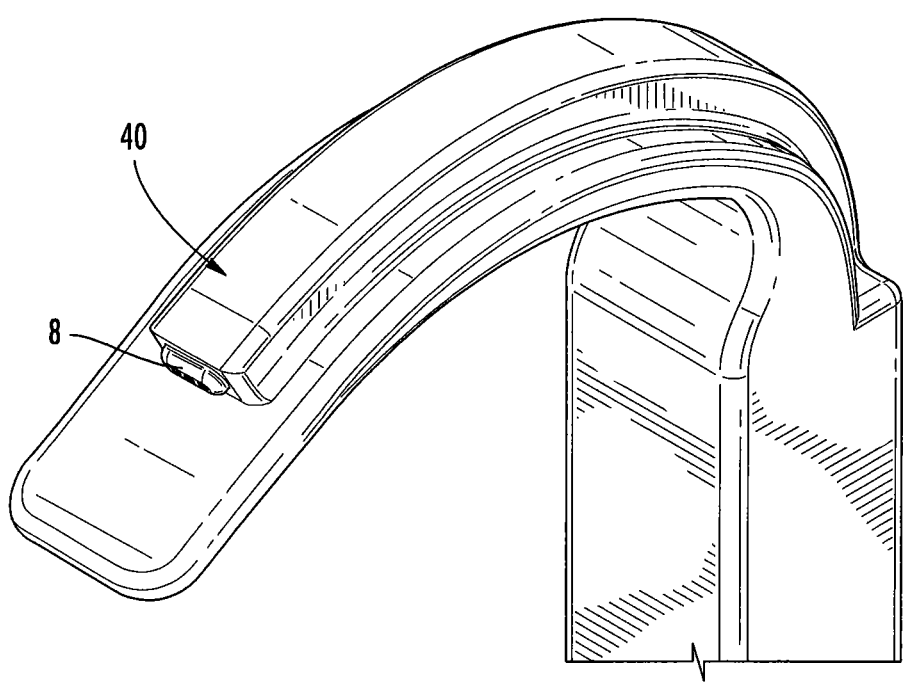
FIG. 2 is a detail perspective view of a protected covering shield portion of an exemplary embodiment of the present invention.
Figure 3A:
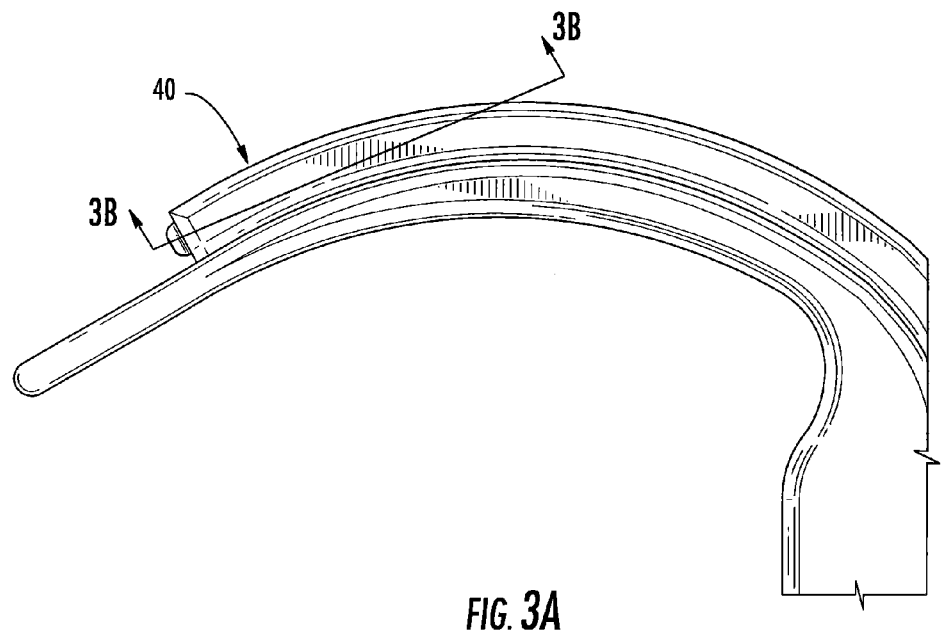
FIG. 3A is a side view of the protected covering shield portion of FIG. 2.
Figure 3B:
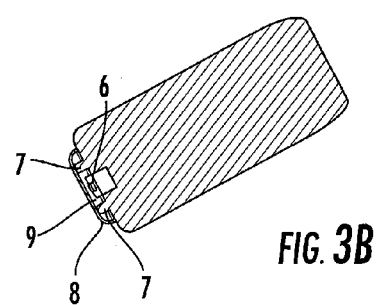
FIG. 3B is a cross sectional view of the protected covering shield with a camera and lighting elements of an exemplary embodiment of the present invention taken along line 3B-3B of FIG. 3A.
Figure 4:
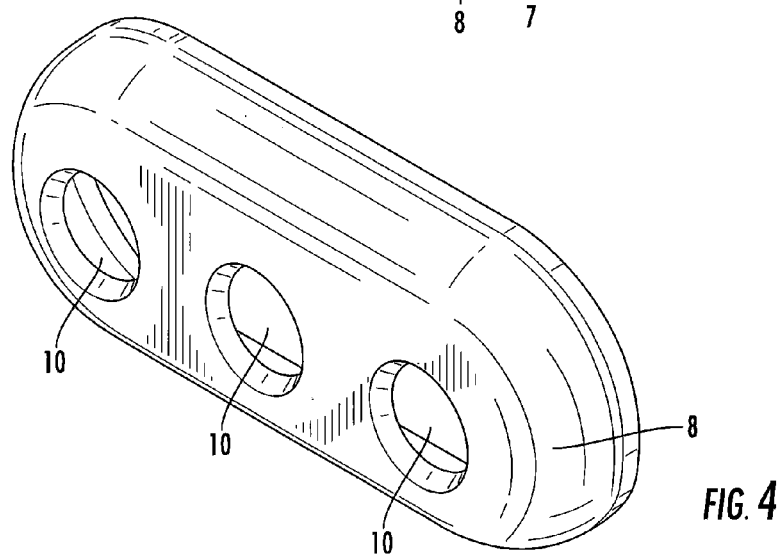
FIG. 4 is a detail perspective view of the protected covering shield portion of an exemplary embodiment of the present invention.

As is illustrated in FIGS. 1 through 4, a video laryngoscopy device may have an overall length of from about 1 to about 6 feet depending upon cable length, and can be made, at least in part, of plastic enclosures, and the like, combined with electronics. Portions of the device may be made with other suitable rigid materials. The device may include a blade 1, a cable 2, and a screen module 3. The blade 1 may include a handle portion 4, a curved or straight blade portion 5, an internal camera module 6 and lighting elements 7. The handle portion 4 may be straight or may be curved to fit a user's hand. In some embodiments, the blade 1 may also have a retention feature for holding the screen module 3 when the user desires to attach the screen module 3 to the blade 1. The curved or straight blade portion 5 may vary in length and width based on patient size. The internal camera module 6 and lighting elements 7 may be fully or partially enclosed by a protected or protective cover shield 8. The protective cover shield 8 may have flat surfaces. In certain embodiments, the protective cover shield 8 may have curved surfaces. In either embodiment, the protective cover shield 8 may include at least one void 10 where direct lighting or direct image sensing can be achieved without obstruction from the protective cover shield 8 itself. An inner chamber 9, as shown in FIG. 3, may provide an air gap which can accommodate and divert any unwanted debris or material that enters into the chamber. In some embodiments, a transparent window acts as the protective covering shield 8. The transparent window can have flat or curved surfaces. In some embodiments, the shield can be made of semi-transparent material that can act to diffuse the light with a void 10 in the protective cover shield 8 for direct image sensing. The lighting elements 7 can be LEDs in the visible and infrared spectrum. Alternately, the lighting elements 7 can be LEDs of a combination of desired wavelengths. A number of LEDs may be used to form a circle or evenly spaced apart or diffused to provide an even distribution of light. The handle portion 4 may include a power source such as batteries or the like to the electronics. Alternately, the batteries can be housed in the screen module 3. The blade 1 may also include a circuit board responsible for amplifying or converting video signals to be passed through the cable 2 to the screen or to a circuit board within the screen module 3 responsible for receiving the video signals and controlling the screen module 3. Either a circuit board in the blade 1 or a circuit board in the screen enclosure may be used to capture a switch or button input signal to power on or off the device. A power switch or button or pull tab or the like may be located on the blade 1 or the cable 2 or the screen module 3. Alternately, a capacitive or resistive touch sensor may be used to power on the unit when touched, with a timeout period in an absence of device usage to power off the unit. The cable 2 may vary in length when manufactured and is responsible for transferring power, video, and any communication signals between the blade 1 and the screen module 3. The screen module 3 may contain a screen such as a TFT or OLED graphic display screen. The screen module 3 may also contain a circuit board module for receiving video signals, receiving input signals, and controlling the graphic display screen. The screen module 3 may also have retention features to allow it to be held by the blade 1 and the screen module 3 may have a clip or mounting bracket for the purpose of a pole holding the screen module 3. The display screen may also have a touchscreen interface controlled by the circuit board. The display screen may also have the ability to rotate the video output based upon position with respect to gravity. A circuit board in the blade 1 or screen module 3 may contain memory for the purpose of transferring recorded video via methods such as SD card, USB, and Firewire. A USB connection may be used to power or recharge the device in some embodiments, and to pass real time video data directly to a PC for video display on a monitor. The device may also pass other video signals out such as composite, component, or HDMI. The device may also contain a microphone to record audio.

In an alternate embodiment, the blade 1 may use some wireless technology such as Bluetooth, or the like, to send video signals to a screen wirelessly and the cable 2 would not exist. In this embodiment, only the blade 1 portion would need to be disposed and would require battery power. In certain embodiments, video may be fed remotely to another location. The blade 1 may include features for assistance in guiding the tube used for intubation such as a guiding channel or attachment features for an external tube guiding mechanism or the like. The device may be used and then disposed of after use.

With roughly 20 million tracheal intubations performed per year in the United States, speed and efficiency are important as many of these intubations are in emergency situations. Video based laryngoscopy is being widely adopted; however, one challenge with video laryngoscope technology is keeping the optics clean throughout the procedure. Optical elements include an image sensor with lens, a lighting element such as an LED, a protective wall, and in some cases fiber optics. The camera field of view and the lighting element field of dispersion should not be impeded by any substance which could directly affect image quality.

Most video laryngoscopes employ a protective covering for the image sensor and lighting elements. When obstructions (such as blood, saliva, etc.) collect on the protective covering, the current procedure is to retract the device and manually wipe the area clean prior to reinsertion and repositioning. As such, there is a need for improving on existing technology to either keep the field of view from being obstructed, or to clean the field of view without having to retract the device.

Figure 5:
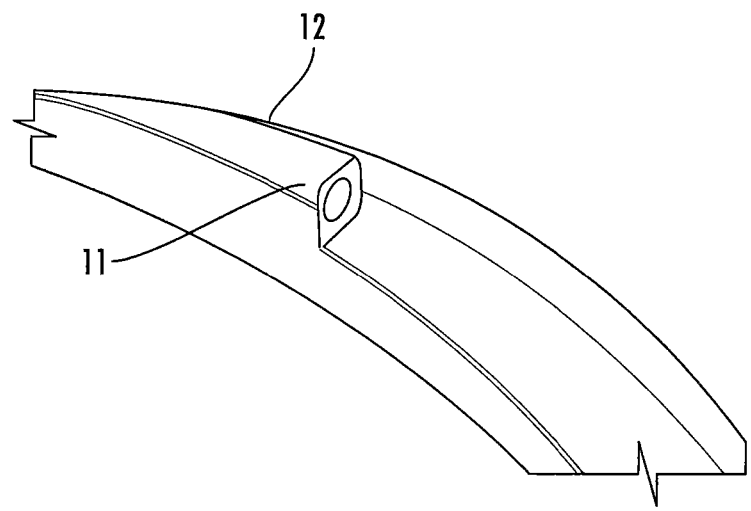
FIG. 5 is a fragmentary perspective view of a pocket area and sidewall of some known video laryngoscopes.

It is easy for obstructions to collect in pocket areas, which may even prove difficult to wipe off in some instances. FIG. 5 shows an example of many typical blades. As can be seen by the figure, there is a pocket area 11 right in front of the lighting or image sensing elements. This is in part due to the sidewall 12 which could have the purpose of extra support, assisting with sensor/lighting area clearing the teeth, or helping to slide some object to the side without directly impacting the sensor/lighting area. However, the opposite top edge of the pocket 11 is still often caught on the teeth during insertion.

The protective covering for the optical elements is generally a flat rectangular window made of glass or plastic. Some devices use a thermistor in conjunction with heating elements to provide an anti-fog feature for any reduction in image quality due to potential condensation build up on the window itself.

Figure 6:
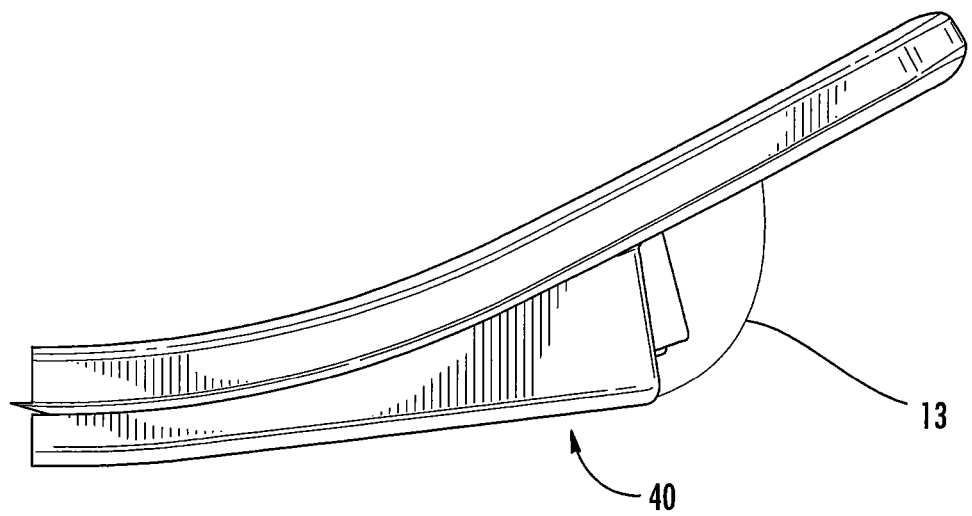
FIG. 6 is a side view of a protected covering shield portion in the form of a rounded dome in accordance with an exemplary embodiment of the present invention.

One way to improve on existing architecture is to employ a rounded or half dome shape protective covering 13, or "shield" as shown in FIG. 6. This shield could act to completely enclose the optical elements. In some embodiments, additives could act to prevent substances from adhering to the external surface of the shield. Also, barriers could be used to direct light or reduce unwanted reflections.

Figure 7:
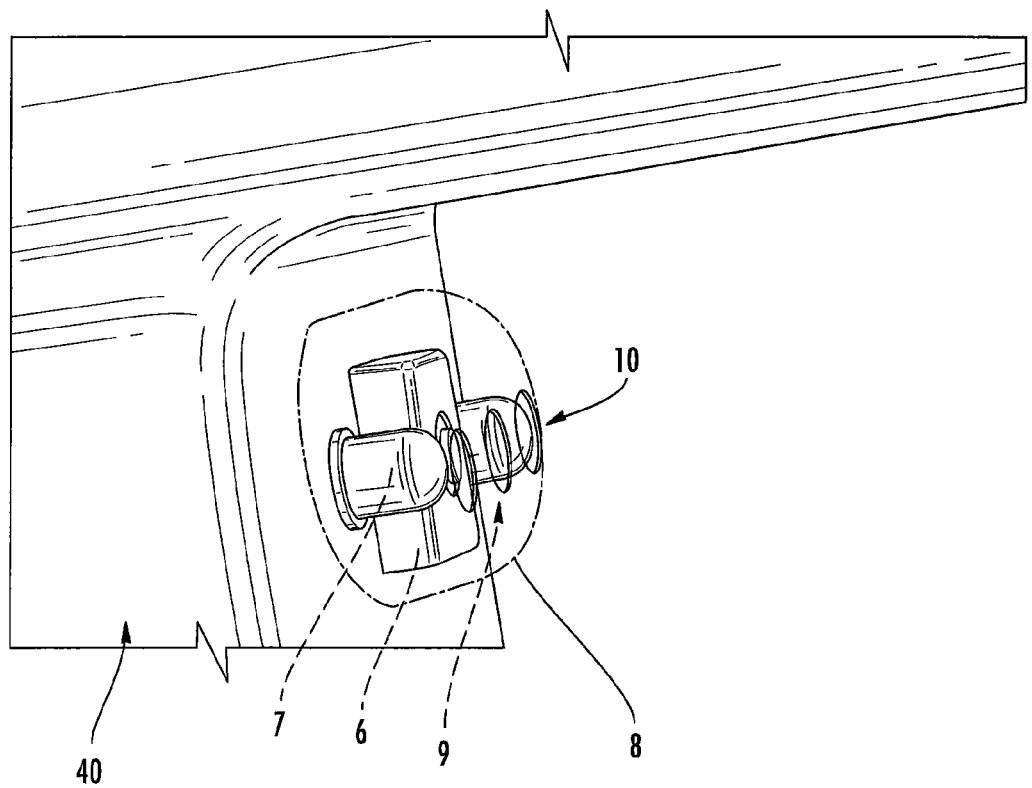
FIG. 7 is a fragmentary perspective view illustrating a protected covering shield portion of an exemplary embodiment of the present invention.

As generally described above in reference to FIGS. 3 and 4, another way to improve on existing architecture is to implement a shield 8 which could employ either a baffle approach or voids/holes 10 in the shield. The shield could also have an inner chamber 9 providing an air gap between the external shield wall and the optical elements. This could be employed in a single use disposable blade without the need of cleaning optical elements after use. This approach could provide the best image quality by allowing the image sensor 6 with lens to have a direct line of site without an extra impeding window, although any protective window should be made to be as transparent as possible. One example of such a shield is shown in FIG. 7. It may still be desirable to use a protective covering "window" to fully enclose the optical elements in conjunction with the external shield.

Figure 11:
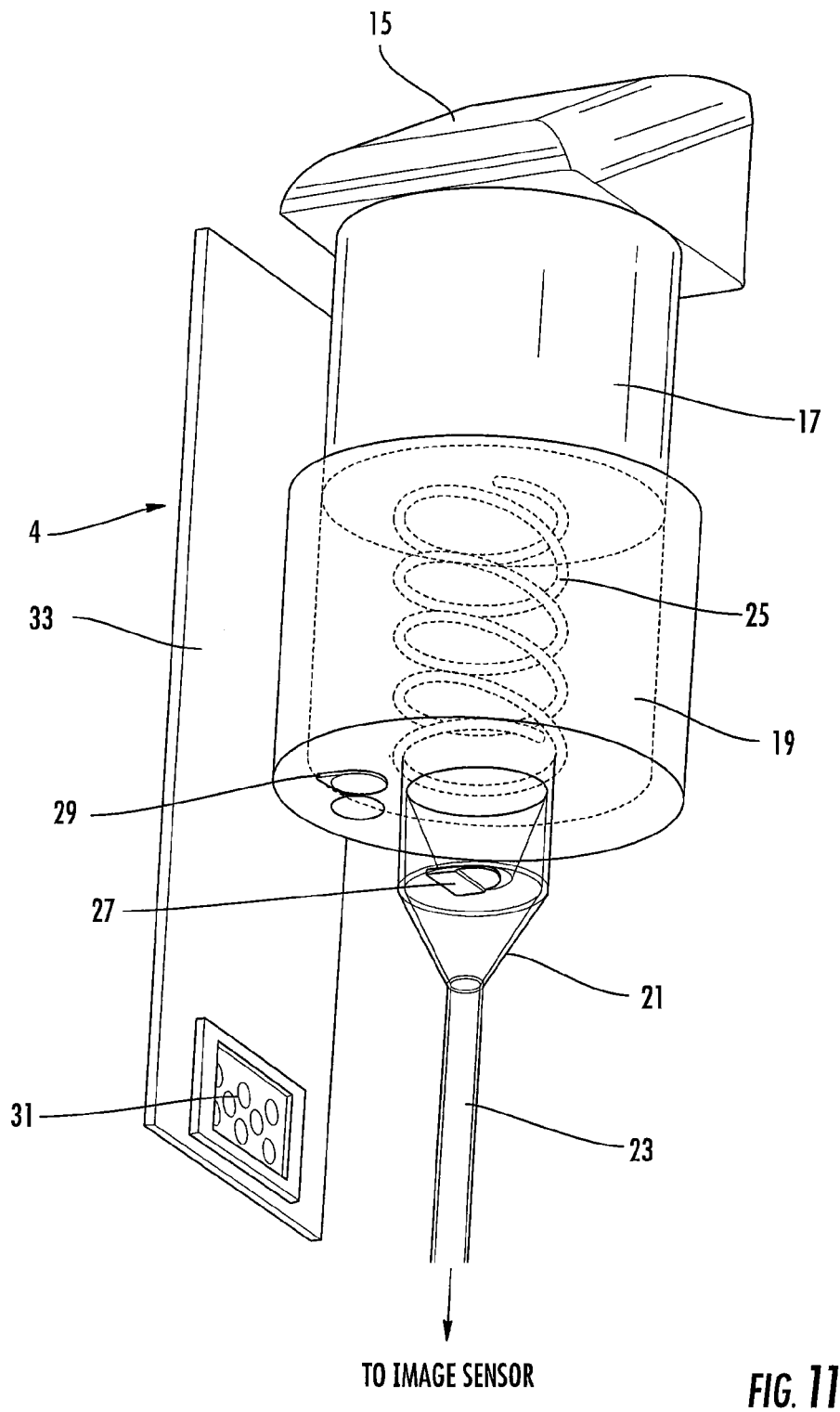
FIG. 11 is an exploded view of a protected covering shield and/or image sensor cleaning assembly in accordance with an exemplary embodiment of the present invention.

It could be of concern that substances could enter or become stuck in the baffle or voids of the shield shown in FIG. 7. In some embodiments, a quick burst of air could be directed in a determined path in order to clean the image sensor lens and/or clear the baffle/void of any substances that might have become stuck or lodged. One possible source for the burst of air could be an actuator 15 (e.g., a simple thumb press button) on a rubber element/switch incorporated into the blade handle 4 as shown in FIG. 11. Check valves could be used to ensure air flow in one direction.

With video laryngoscopes, there is a concern when substances such as saliva, blood and/or vomit become attached to the video laryngoscope directly in front of the camera or image sensor thereby obstructing the view of the image sensor. Normally such debris blocking the image sensor view results in abandoning the current procedure and having to wipe off the debris before reinsertion of the device.

Figure 10:
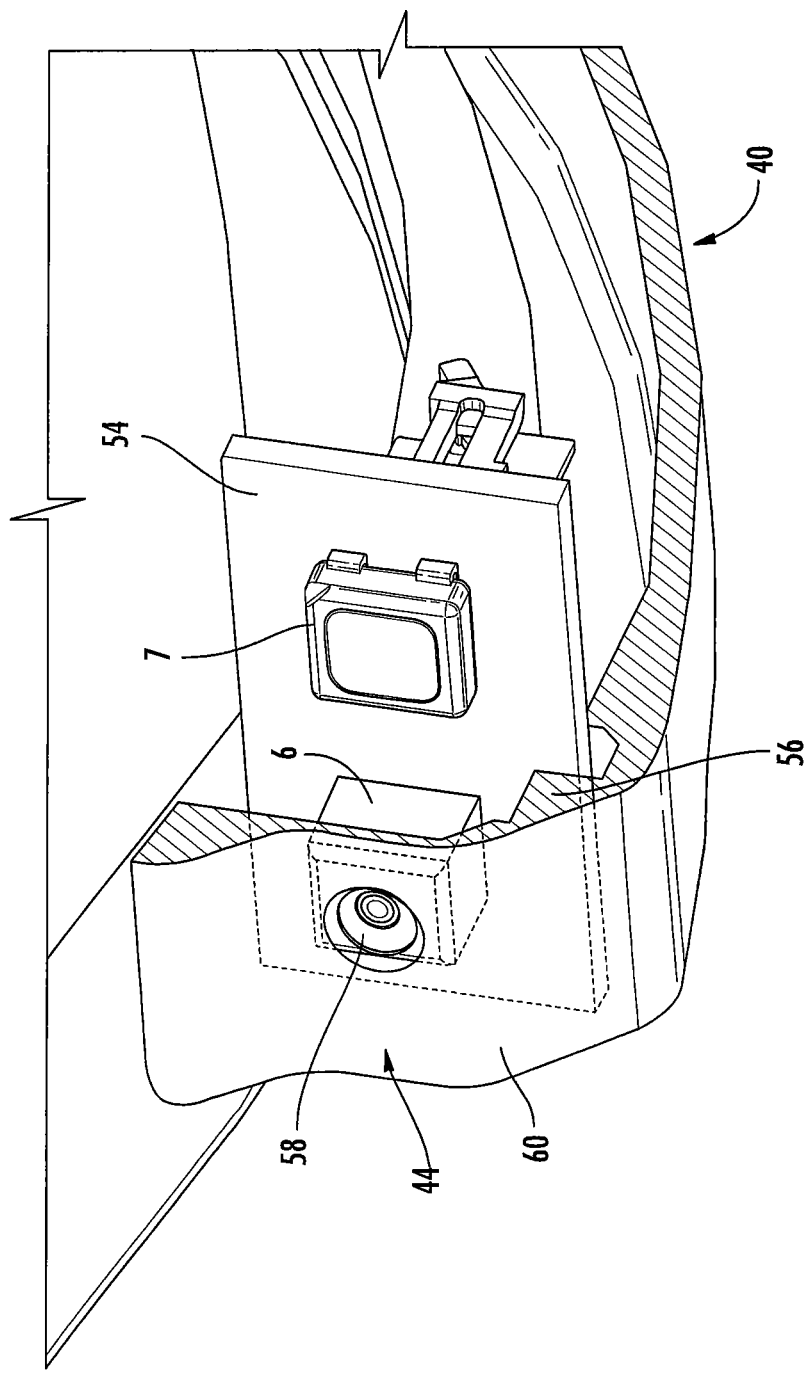
FIG. 10 is a fragmentary perspective sectional view illustrating the electronics housing of FIG. 8 and electronics housed therein in accordance with an exemplary embodiment of the present invention.

Referring to FIG. 11, according to some embodiments, a quick burst of air can be directed in a predetermined path in order to clean the image sensor lens area of any substances that may have become stuck or lodged. The actuation of the quick burst of air may be carried out using an actuator such as a thumb press button 15 located on the handle portion 4 of the video laryngoscope device. By pressing the thumb button 15, a plunger 17 translates into a volume of air in an air reservoir such as a cylinder 19 causing the air to be funneled into a smaller diameter channel 21 acting as a high velocity air nozzle and through tubing 23 that is in fluid communication with an area around the image sensor. In particular, a distal end of the tubing 23 could terminate at or near the image sensor 6 and/or the inner chamber 9 (FIG. 7), at or near the domed protective covering shield 13 (FIG. 6), or at or near the image sensor 6 (FIG. 10). The tubing 23 may extend through the handle 4 and/or the blade 5 of the video laryngoscope. Additionally, the tubing may extend through an electronics housing that is described in more detail below. The tubing 23 may terminate very close to the image sensor lens and/or the protective covering shield at the side or at an angle to blow off any debris thereon. A more forceful actuation of the button 15 would increase the pressure in the cylinder 19 thereby causing the air to flow at an even greater velocity to clear the small image sensor lens (or protective covering shield). A spring 25 in the cylinder 19 forces the plunger 17 and button 15 back to its normal position after the button 15 is released.

A first one-way valve such as a check valve 27 (e.g., with a plastic flap) may be used to ensure that the air flows in only one direction. That is, the first check valve 27 ensures that air is only directed from the cylinder 19 through the nozzle 21 toward the image sensor lens when the button 15 is pressed. A second one-way valve such as a check valve 29 may be used to ensure that external air enters the cylinder 19 when the button 15 is returned by the spring 25 to its normal position. For example, a filter 31 may be provided on a sidewall 33 of the handle 4. The second check valve 29 ensures that the external air enters the cylinder 19 through the filter 31 when the button 15 is returned by the spring 25 to its normal position. That is, new air only comes externally though the filter 31 to fill the cylinder 19. The second check valve 29 also ensures that air does not exit the filter 31 when the button 15 is pressed.

Figure 8:
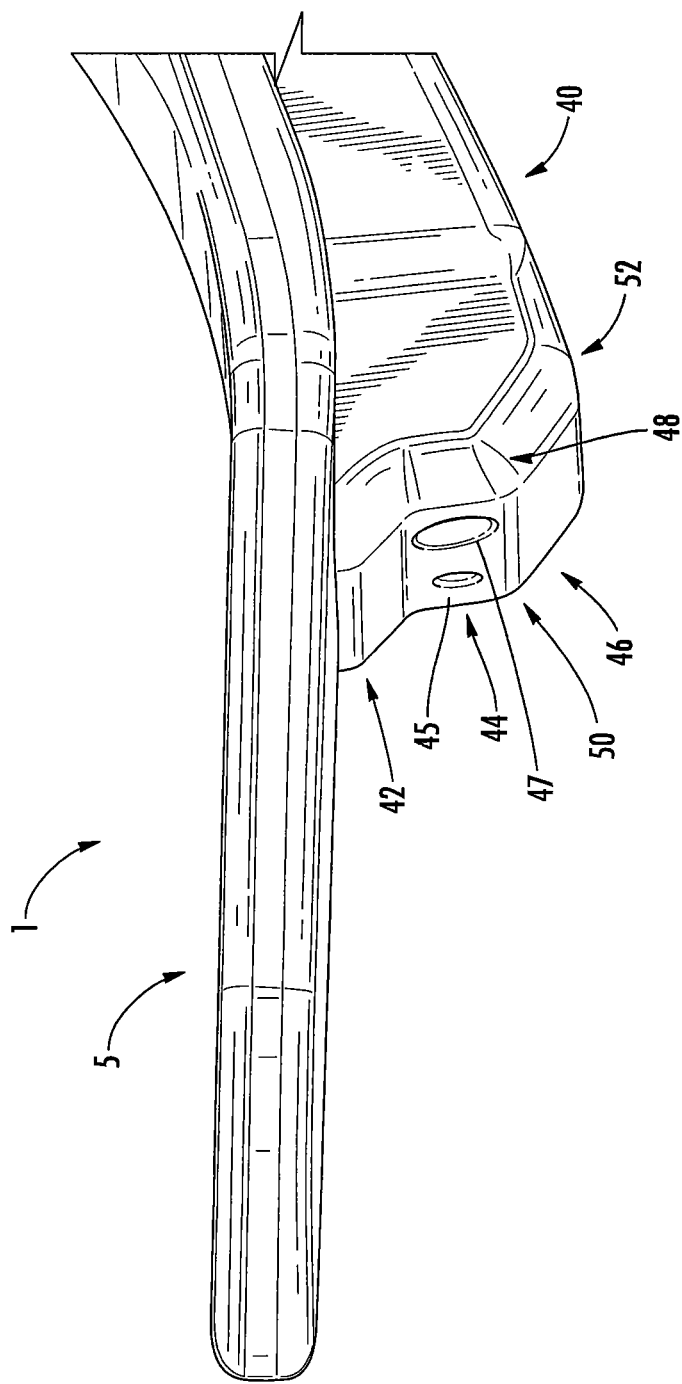
FIG. 8 is a fragmentary perspective view illustrating an electronics housing of an exemplary embodiment of the present invention.
Figure 9:
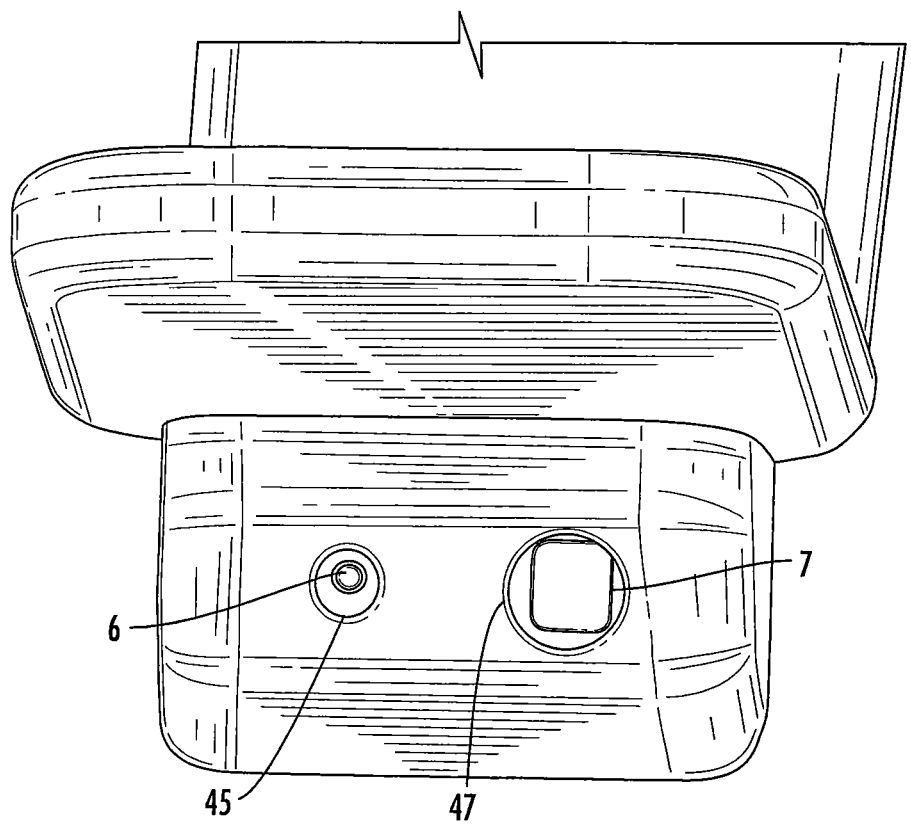
FIG. 9 is a fragmentary end view illustrating the electronics housing of FIG. 8.

Another embodiment is shown in FIGS. 8-10. The blade 1 may include an electronics housing portion 40 that extends away from the blade portion 5. According to some embodiments, the electronics housing 40 is integrally formed with the blade portion 5. The electronics housing 40 houses the camera or image sensor 6 and the lighting element or LED 7 (FIGS. 9 and 10).

As viewed in FIG. 8, the electronics housing 40 may include a first ramp portion or surface 40 that extends downwardly away from the blade portion 5 and away from a distal end of the blade portion 5, a straight portion or surface 44 that extends downwardly away from the first ramp portion 42, and a second ramp portion or surface 46 that extends downwardly away from the straight portion 44 and away from the distal end of the blade portion 5. On each side is a rounded taper portion or surface 48. There may also be rounded portions or surfaces 50 between the blade 5 and the first ramp portion 42, between the first ramp portion 42 and the straight portion 44, between the straight portion 44 and the second ramp portion 46, and/or between the second ramp portion 46 and a lower portion or surface 52. In this regard, the "leading edge" of the electronics housing may be comprised of completely or substantially completely rounded surfaces, thereby facilitating easier insertion during use of the video laryngoscope. It will be understood that the terms "downwardly" and "lower" are used to clearly describe the device as illustrated in FIG. 8. In use, the blade 5 depresses the tongue and the electronics housing 40 is toward the top of the mouth cavity upon insertion.

The straight portion 44 may include apertures 45, 47 defined therein. The aperture 45 may be aligned with the image sensor 6 and the aperture 47 may be aligned with the lighting element 7.

Referring to FIG. 10, the camera or image sensor 6 and the lighting element 7 may be mounted on a substrate 54 within the electronics housing 40. The electronics housing 40 may include a partition 56 that isolates or separates the image sensor 6 and the lighting element 7. In this regard, light from the lighting element 7 may be directed in the proper direction and not illuminate the area immediately adjacent the image sensor 6.

The camera or image sensor 6 may be a cube camera and may extend further from the substrate than does the lighting element 7. In some embodiments, the camera lens 58 may be flush or proud with a front surface 60 of the straight portion 44. In some embodiments, the camera lens 58 may be used as the protective window. In some embodiments, the straight portion 44 and/or the front surface 60 thereof surrounds the camera lens 58.

It is noted that the embodiments illustrated in FIGS. 1-4, 6 and 7 may also include the electronics housing 40 extending from the blade portion 5.

Various embodiments described herein allow the user of the video laryngoscope to maintain visibility without device retraction and manual cleaning in the majority of cases where device retraction, cleaning, and reinsertion would normally be necessary.

It will be understood that when an element is referred to as being "coupled" or "connected" to another element, it can be directly coupled or connected to the other element or intervening elements may also be present. In contrast, when an element is referred to as being "directly coupled" or "directly connected" to another element, there are no intervening elements present. Like numbers refer to like elements throughout. As used herein the term "and/or" includes any and all combinations of one or more of the associated listed items.

Many different embodiments have been disclosed herein, in connection with the above description and the drawings. It will be understood that it may be unduly repetitious and obfuscating to literally describe and illustrate every combination and subcombination of these embodiments. Accordingly, the present specification, including the drawings, shall be construed to constitute a complete written description of all combinations and subcombinations of the embodiments described herein, and of the manner and process of making and using them, and shall support claims to any such combination or subcombination.

It should be understood, of course, that the foregoing relates to exemplary embodiments of the invention and that modifications may be made without departing from the spirit and scope of the invention as set forth in the following claims.

What is claimed is:

1. A video laryngoscopy device comprising:
   a blade having a handle and a blade portion extending from the handle;
   an electronics housing extending from the blade portion; and
   a camera or image sensor and a lighting element housed within the electronics housing;
   wherein the device is single use disposable;
   wherein the electronics housing comprises:
      a first rounded portion extending downwardly away from a surface of the blade portion;
      a first ramped portion extending downwardly away from the first rounded portion and proximally away from a distal end of the blade portion;
      a second rounded portion extending downwardly away from the first ramped portion;
      a straight portion extending downwardly away from the second rounded portion and including a first aperture aligned with the image sensor and a second aperture aligned with the lighting element;
      a third rounded portion extending downwardly away from the straight portion;
      a second ramped portion extending downwardly away from the third rounded portion and proximally away from the distal end of the blade portion; and
      a fourth rounded portion between the second ramped portion and a lower surface of the electronics housing.

2. The device of claim 1 wherein the blade is in communication with a display screen, the display screen configured to display video from image data communicated by the blade.

3. The device of claim 2 wherein the blade is in wireless communication with the display screen and is configured to communicate the image data via a Bluetooth wireless connection.

4. The device of claim 1 further comprising a protective cover shield extending away from the electronics housing, the protective cover shield defining a cavity in front of the image sensor and the lighting element.

5. The device of claim 4 wherein at least one hole is defined in the protective cover shield, the at least one hole aligned with at least one of the image sensor and the lighting element.

6. The device of claim 5 wherein the at least one hole comprises a plurality of holes, one each aligned with the image sensor and the lighting element.

7. The device of claim 4 wherein the protective cover shield is dome shaped.

8. The device of claim 7 wherein the protective cover shield comprises additives therein or thereon configured to repel debris.

9. The device of claim 4 further comprising a camera lens cleaning mechanism, the camera lens cleaning mechanism configured to inject air to the image sensor and/or to the cavity to thereby remove debris on a lens of the image sensor.

10. The device of claim 9 further comprising a push button on a top portion of the handle, the camera lens cleaning mechanism configured to inject the air responsive to actuation of the push button.

11. The device of claim 10 wherein the camera lens cleaning mechanism comprises an air reservoir, a nozzle connected to the air reservoir and tubing connected to the nozzle and terminating at or adjacent the image sensor and/or the cavity, wherein air from the air reservoir is injected through the nozzle and through the tubing responsive to actuation of the push button.

12. The device of claim 11 wherein the camera lens cleaning mechanism further comprises a first check valve disposed between the air reservoir and the nozzle, the first check valve configured to allow the flow of air toward the image sensor and/or to the cavity through the tubing and prevent the flow of air in the opposite direction.

13. The device of claim 11 further comprising:
a filter on a sidewall of the handle; and
a second check valve on a bottom portion of the air reservoir;
wherein the second check valve is configured to allow the flow of air from outside the handle through the filter into the air reservoir and prevent the flow of air in the opposite direction.

14. The device of claim 1 wherein the image sensor and the lighting element are held on a substrate in the electronics housing, the electronics housing comprising a partition member between the image sensor and the lighting element.

15. The device of claim 1 wherein the image sensor is a cube camera that extends further away from the substrate than does the lighting element.

16. The device of claim 15 wherein the cube camera comprises a lens that is substantially flush with a front surface of the straight portion.

* * * * *